United States Patent
Temkin et al.

(10) Patent No.: US 6,625,249 B1
(45) Date of Patent: Sep. 23, 2003

(54) METHOD, SYSTEM AND PROGRAM PRODUCT FOR TOMOGRAPHIC BACKPROJECTION USING MULTI-COLOR RENDERING ENGINE

(75) Inventors: Joshua M. Temkin, Clifton Park, NY (US); John Schmiederer, Clifton Park, NY (US); Samit Basu, Niskayuna, NY (US)

(73) Assignee: General Electric Company, Niskayuna, NY (US)

( * ) Notice: Subject to any disclaimer, the term of this patent is extended or adjusted under 35 U.S.C. 154(b) by 0 days.

(21) Appl. No.: 10/251,726

(22) Filed: Sep. 20, 2002

(51) Int. Cl.[7] ............................................. A61B 6/03
(52) U.S. Cl. ............................ 378/4; 378/15; 378/901
(58) Field of Search ........................... 378/4, 8, 15, 19, 378/901

(56) References Cited

U.S. PATENT DOCUMENTS

| | | | |
|---|---|---|---|
| 6,002,738 A | 12/1999 | Cabral et al. ................... | 378/4 |
| 6,163,617 A | 12/2000 | Heuscher et al. ............ | 382/132 |

OTHER PUBLICATIONS

B. Cabral, N. Cam, & J. Foran, "Accelerated Volume Rendering and Tomographic Reconstruction using Texture Mapping Hardware," 1994 Symposium on Volume Visualization, pp. 91–98, ACM SIGGRAPH, Oct. 1994.

K. Mueller, Yagel, R., "On the Use of Graphics Hardware to Accelerate Reconstruction Methods," 1999 SPIE Medical Imaging Conference, No. 3569–62, San Diego, CA Feb.

H. Turbell, "Three–Dimensional Image Reconstruction in Circular and Helical Computed Tomography," Department of Electrical Engineering, Linkopins Universitet, Thesis No. 760, pp. i–85, Linkoping, Sweeden, Apr. 1999.

*Primary Examiner*—David V. Bruce
(74) *Attorney, Agent, or Firm*—Heslin Rothenberg Farley & Mesiti P.C.; Kevin P. Radigan, Esq.

(57) ABSTRACT

Method, system and program product are provided implementing a technique for backprojecting an image from a projection data set. The technique includes splitting the projection data set into a plurality of multi-channel textures, with each multi-channel texture corresponding to a predetermined number of color channels of a multi-color rendering engine. The multi-color rendering engine is employed to simultaneously render the split projection data set and obtain intermediate results for each color channel. The intermediate results of each color channel are then accumulated to generate separate rendered images, wherein multiple images are simultaneously rendered from the projection data set using the separate color channels of the multi-color rendering engine.

42 Claims, 6 Drawing Sheets

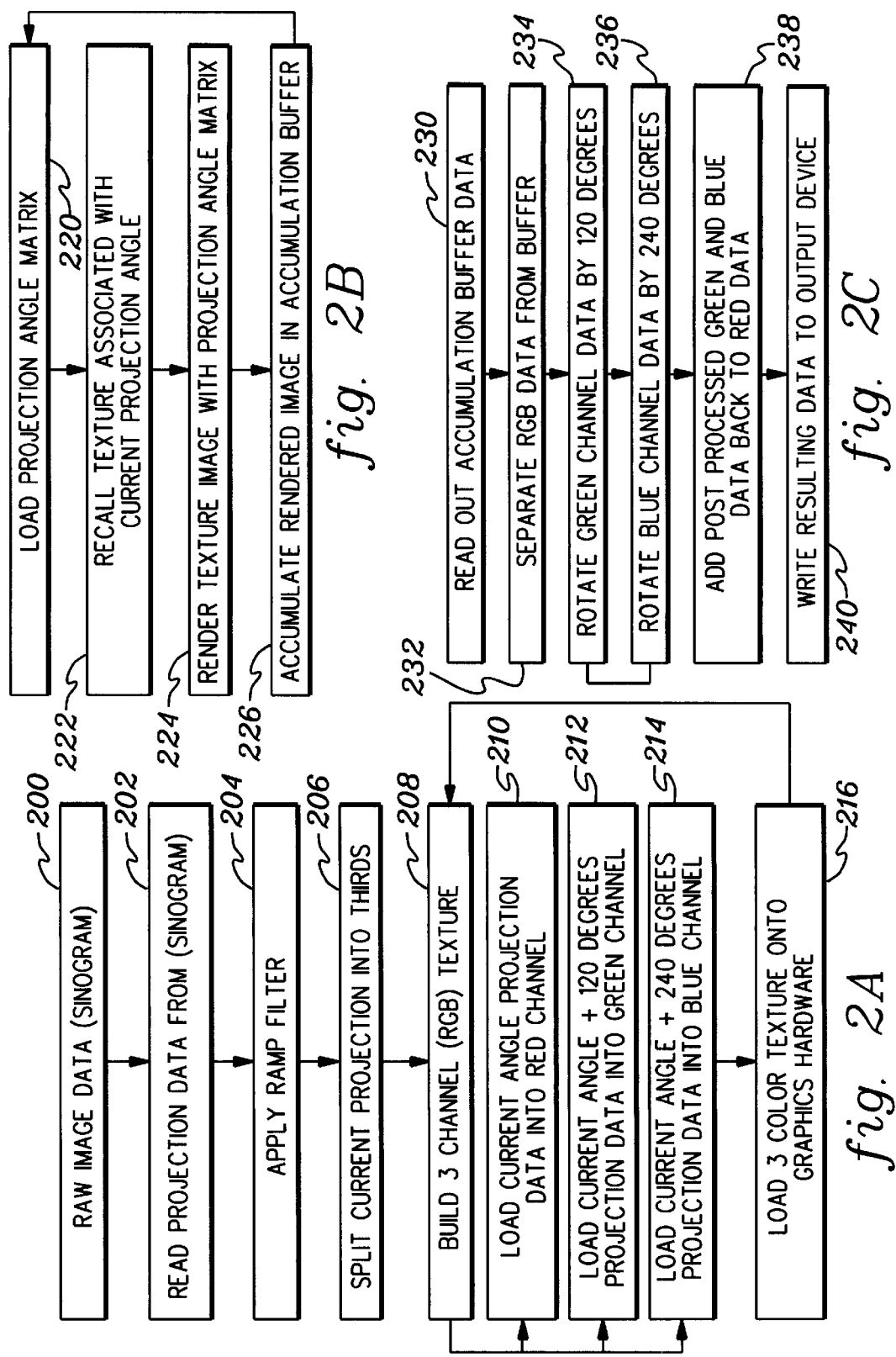

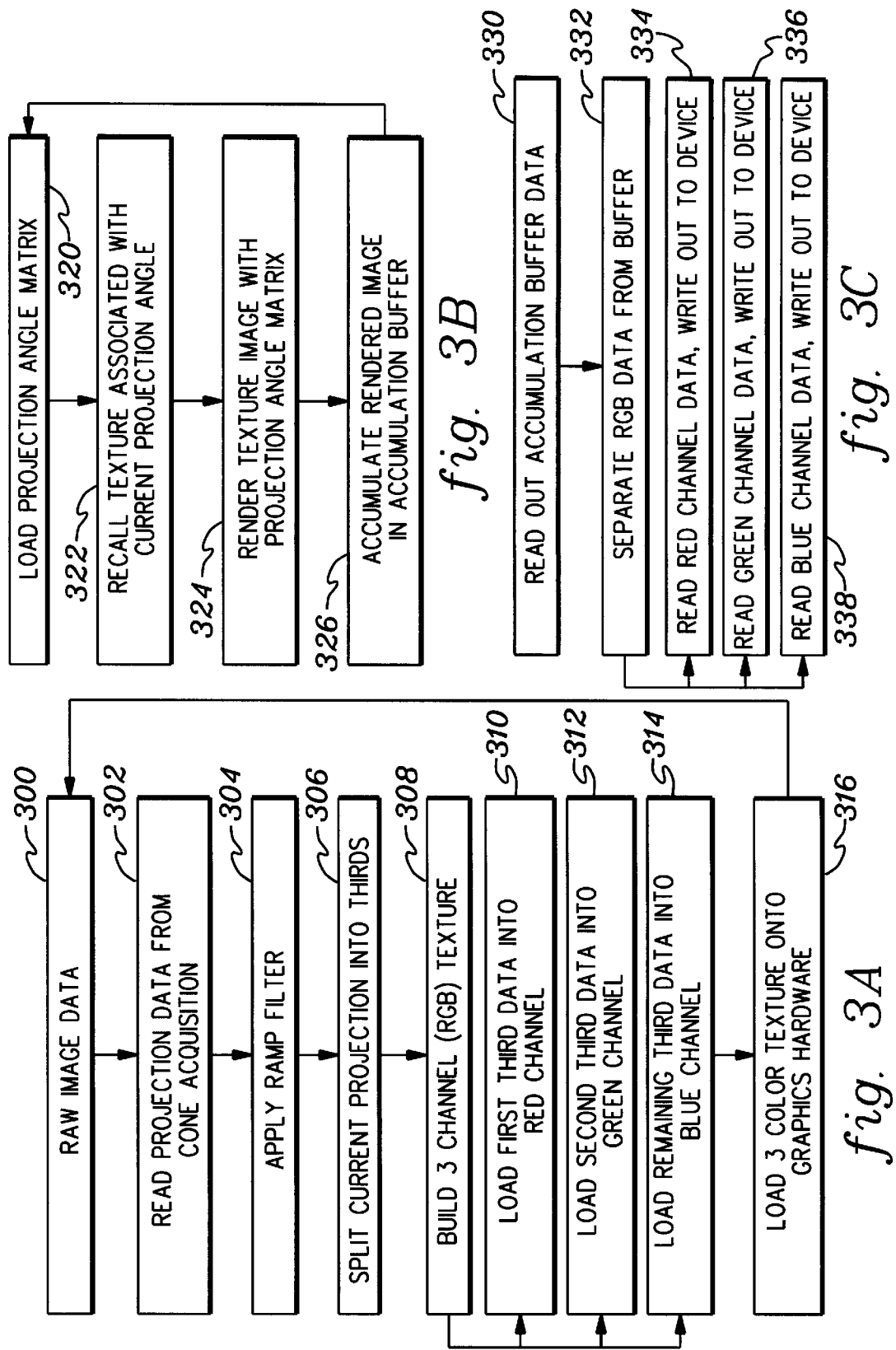

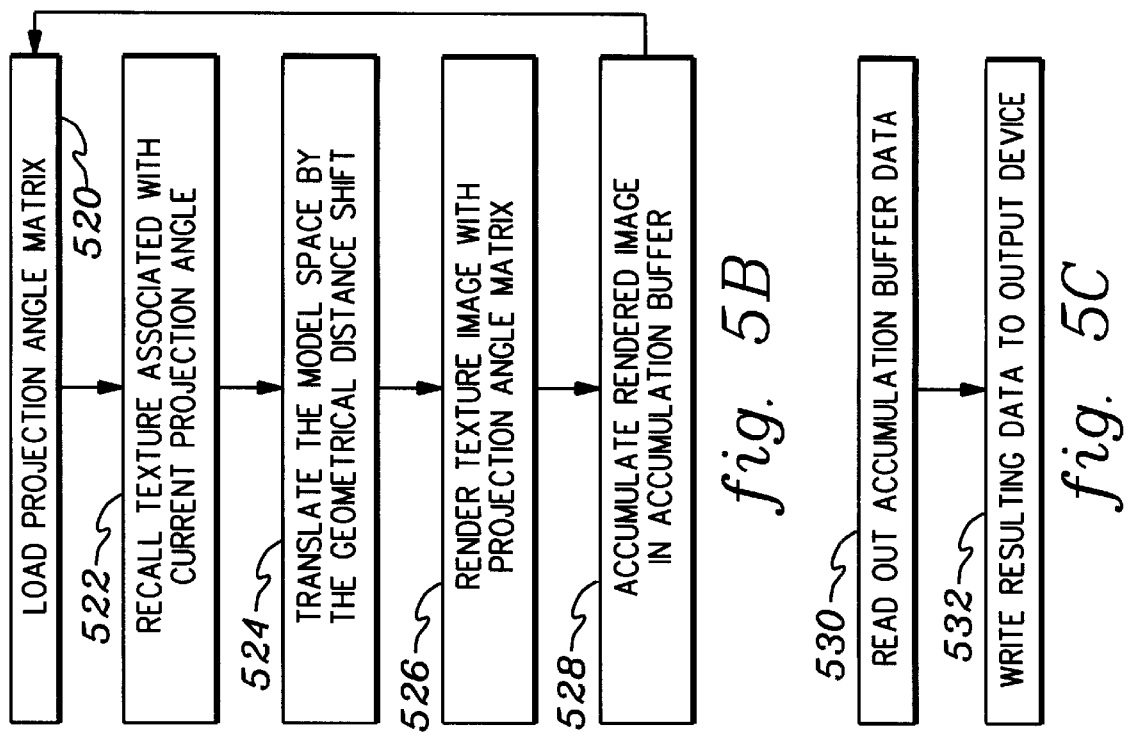
fig. 5B
fig. 5C
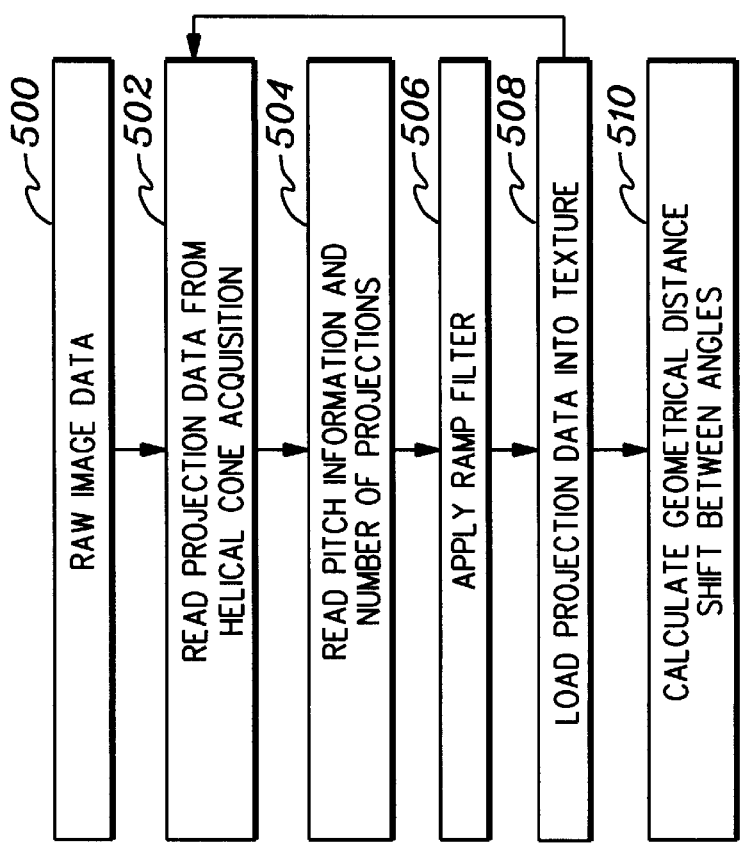
fig. 5A

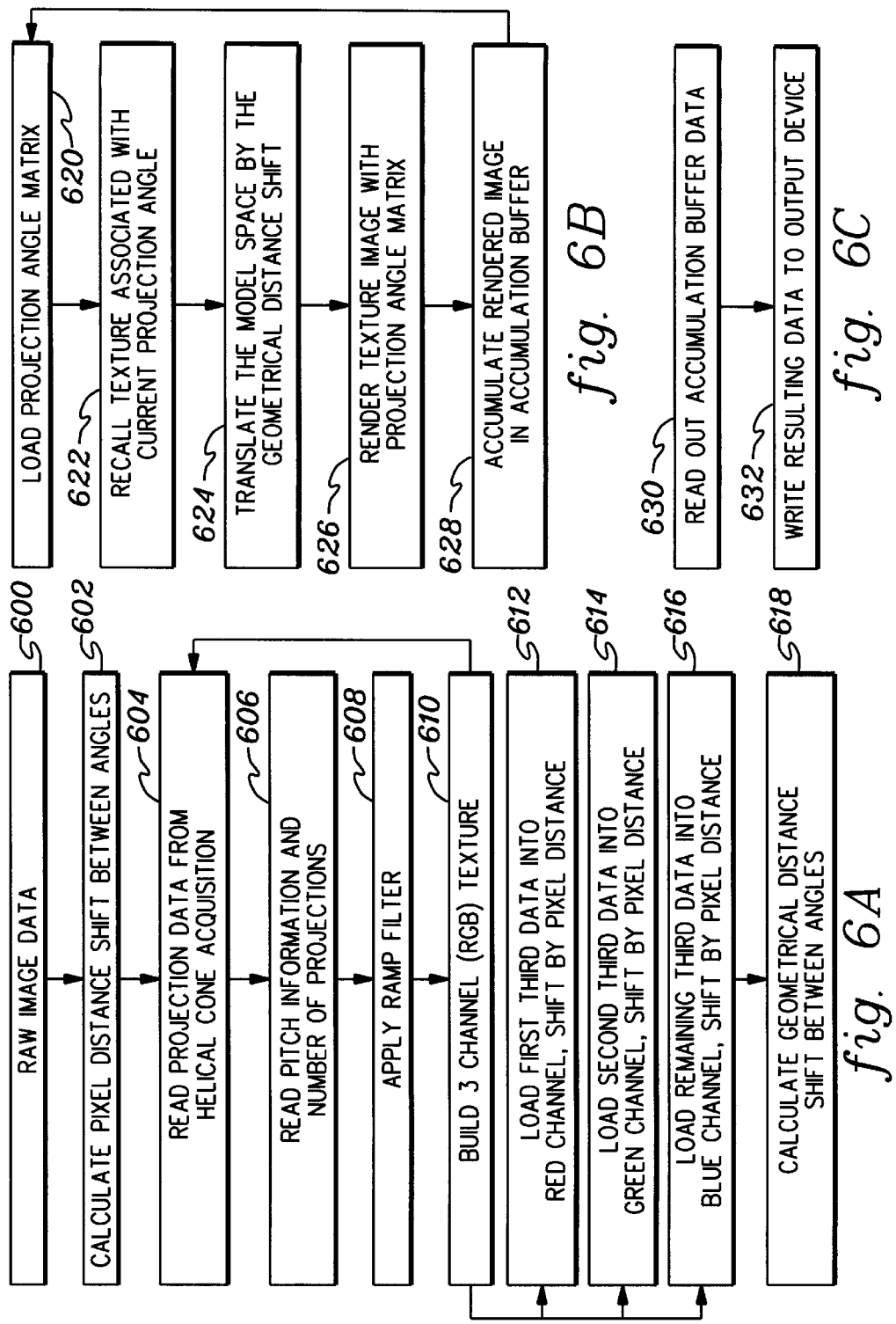

METHOD, SYSTEM AND PROGRAM PRODUCT FOR TOMOGRAPHIC BACKPROJECTION USING MULTI-COLOR RENDERING ENGINE

BACKGROUND OF THE INVENTION

The present invention relates to the field of computer tomography, and more particularly, to tomographic backprojection and volume rendering using a multiple color channel, graphics rendering engine.

Volume visualization of real-time or recorded images encompasses not only viewing, but also construction of a volumetric data set from the more basic projection data obtained from a sensor source. Most volumes used in rendering are derived from such sensor data. A primary example being computer aided tomographic (CAT) x-ray data. This data is usually a series of two dimensional projections of a three dimensional volume. The process of converting this projection data back into a volume is called tomographic backprojection. The term tomographic backprojection or computer tomography (CT) is used to differentiate it from signal reconstruction; i.e., the rebuilding of a continuous function (signal) from a discrete sampling of that function. Once a slice or volume is tomographically reconstructed, it can be visualized using known rendering techniques.

Computer tomography (CT) provides an image representing a transfer slice (also referred to as a plane) of a body or an object. This slicing is accomplished by rotating an x-ray source into the detection means (e.g., a row (ID) or array (2D) of sensors) around the perimeter of the section of the body or object to be viewed. The source and detection means are typically placed 180° from each other to allow the detection means to measure the attenuation of the beam as it passes through the plane (slice) of interest. When enough measurements have been taken, a computer system is utilized to mathematically interpret the data, which is then displayed as a slice or an entire volume (volume rendering) on a monitor (e.g., a computer screen) for diagnostic or control purposes.

The operations of tomographic backprojection and volume rendering have traditionally been commercially implemented by specialized, very expensive CT systems. Medical procedures that require this hardware are likewise expensive, in some cases limiting patient accessibility to such procedures. Therefore, a need exists in the art for an enhanced method, system and program product for performing these operations in a more efficient, less costly manner.

Tomographic backprojection using conventional graphics hardware has been performed in the art. For example, reference an article by Cabral et al. entitled "Accelerated Volume Rendering and Tomographic Backprojection Using Texture Mapping Hardware," 1994 Symposium on Volume Visualization, pp. 91–98, ACM SIGGRAPH, October 1994, as well as U.S. Pat. No. 6,002,738. Presented herein are various enhancements to the general backprojection approaches described, for example, by Cabral et al.

SUMMARY OF THE INVENTION

The present invention provides, in one aspect, a method of image backprojection from a projection data set. This method includes: splitting the projection data set into a plurality of multi-channel textures, each multi-channel texture corresponding to a predetermined number of color channels of a multi-color rendering engine; simultaneously rendering the split projection data set using the color channels of the multi-color rendering engine to obtain intermediate results for each color channel; and accumulating the intermediate results of each color channel to generate separate rendered images, wherein multiple images are simultaneously rendered from the projection data set using the separate color channels of the multicolor rendering engine.

In another aspect, a diagnostic imaging method is provided which includes generating a projection data set, and reconstructing an image from the projection data set. The reconstructing includes: splitting the projection data set into a plurality of multi-channel textures, each multi-channel texture corresponding to a predetermined number of color channels of a multi-color rendering engine; simultaneously rendering the split projection data set using the color channels of the multi-color rendering engine to obtain intermediate results from each color channel; and accumulating the intermediate results of each color channel to generate separate rendered images, wherein multiple images are simultaneously rendered for the projection data set using the separate color channels of the multi-color rendering engine.

In still another aspect, a method of image backprojection from helical beam projection data is provided. Unless otherwise specified, helical beam projection data is used herein to refer to helical fan beam and/or helical cone beam projection data. The method includes: loading the projection data into multiple textures; for at least one texture, determining a texture distance change between pitch angles using at least some textures of the multiple textures; rendering the multiple textures using a graphics rendering engine, the rendering including adjusting a model space for rendering texture data associated with at least one projection angle for a constant texture distance using the determined texture distance change between pitch angles; and accumulating rendered images to produce a reconstructed image from the helical beam projection data.

In a further aspect, a diagnostic imaging method is provided which includes generating helical beam projection data and reconstructing an image from the helical beam projection data. The reconstructing includes: loading the projection data into multiple textures; for at least one texture, determining a texture distance between pitch angles using the at least some textures of the multiple textures; rendering the multiple textures using a graphics rendering engine, the rendering including adjusting a model space for rendering texture data associated with at least one projection angle for a constant texture distance using the determined texture distance change between pitch angles; and accumulating rendered images to produce a reconstructed image from the helical beam projection data.

Systems and computer program products corresponding to the above-summarized methods are also described and claimed herein. Further, other embodiments and aspects of the invention are also described in detailed and claimed.

BRIEF DESCRIPTION OF THE DRAWINGS

The present invention may take form in various components and arrangements of components, and in various steps and arrangement of steps. The drawings presented herewith are for purposes of illustrating certain embodiments and should not be construed as limiting the invention. The subject matter which is regarded as the invention is particularly pointed out and distinctly claimed in the claims at the conclusion of the specification.

FIGS. 2A, 2B & 2C are a flowchart of one embodiment of tomographic backprojection processing for a fan beam projection data modality, in accordance with an aspect of the present invention;

FIGS. 3A, 3B & 3C are a flowchart of one embodiment of tomographic backprojection processing for a cone beam projection data modality, in accordance with an aspect of the present invention;

FIGS. 5A, 5B & 5C are a flowchart of one embodiment of a tomographic back projection process for a helical cone beam projection data modality, in accordance with another aspect of the present invention; and FIGS. 6A, 6B & 6C are a flowchart of an alternate embodiment of tomographic backprojection processing for a helical cone beam projection data modality, in accordance with an aspect of the present invention.

DETAILED DESCRIPTION OF THE INVENTION

Figure 1:
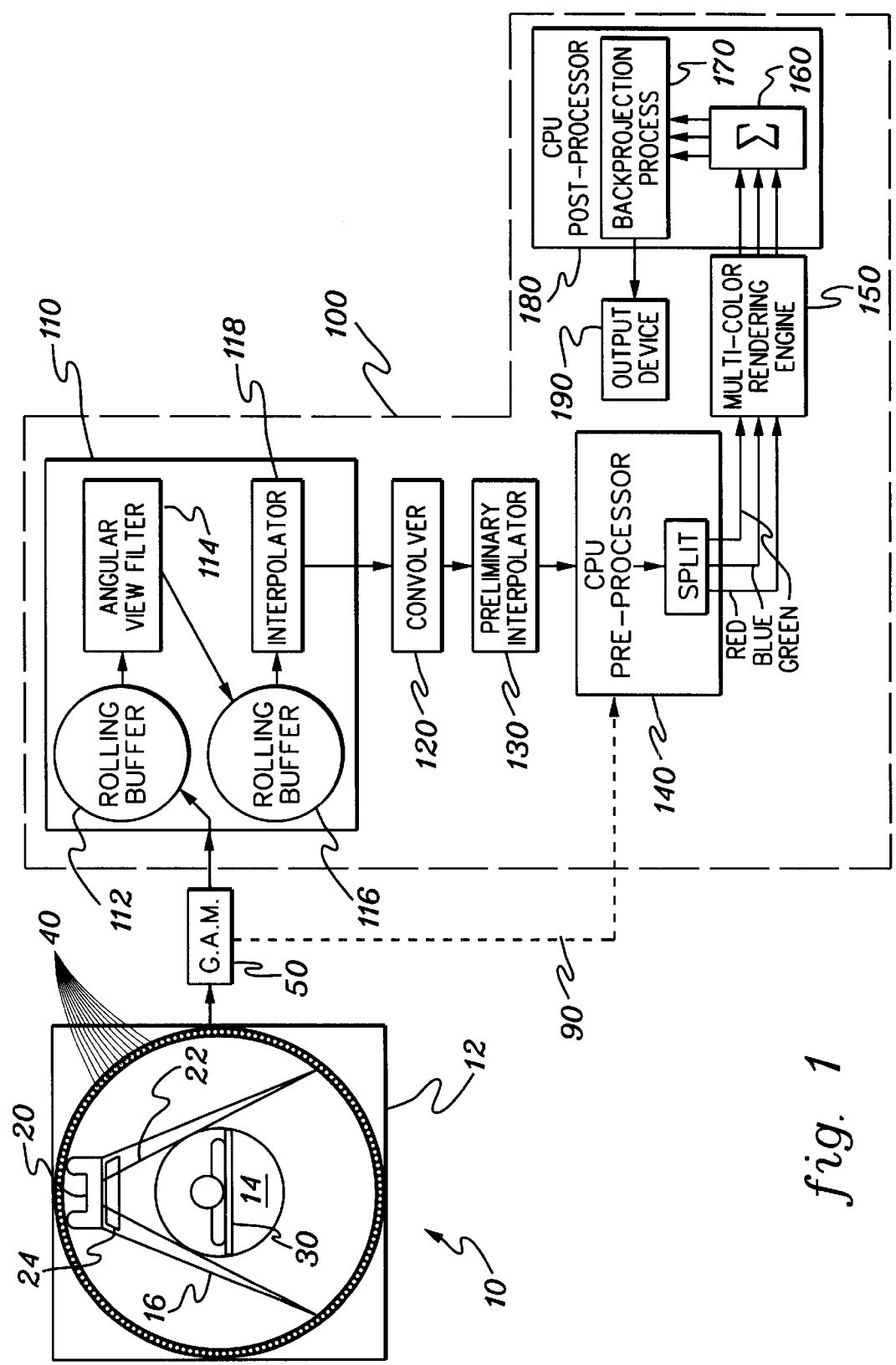
FIG. 1 is a diagrammatic illustration of a CT scanner system employing tomographic backprojection in accordance with one or more aspects of the present invention.

As noted, computerized tomography (CT) uses a set of x-ray projections through an object to reconstruct a density image of the object. Cost effective backprojection of a tomographic image using off-the-shelf components is now feasible. Described herein as a hybrid CPU/graphics card embodiment for accelerating backprojection of CT images, for example, for fan-beam, cone-beam, helical fan-beam, and helical cone-beam acquisitions. More particularly, described herein are hybrid approaches for using, for example, the red, green and blue color channels of an available multi-color rendering engine in combination with CPU bound preprocessing of the raw projection (sinogram) data and post accumulation, back projected image data processing for enhanced performance. Using the concepts presented herein, low cost CPU workstations configured with common off-the-shelf graphics hardware can be employed to reconstruct, for example, fan and cone-beam tomographic images with sub-second backprojection times previously seen only on high-end, dedicated systems. The approaches presented herein can, for example, reduce the time to reconstruct a number of slices to a third of the time otherwise required using the high-end tomographic backprojection approaches available today.

In order to facilitate an understanding of the various aspects of the invention described and claimed herein, the following terms are defined:

Texture—a texture is a precompiled graphics image that is stored in memory associated with a rendering engine, and which can be displayed by rendering (drawing) onto a polygon.

Backprojection—a backprojection is a computational technique for taking a set of projection data images, tracing that data (in a virtual geometry of the original CT system) from the detector back to the source through a volume (in the case of helical cone and cone beam modalities) or across a plane (in the case of fan beam), depositing the values from each pixel in each individual projection image at the angle at which the projection image was acquired during the original scan, and accumulating all of the backprojected data onto a new slice. The total accumulation of all the projection data at the angles they were acquired results in the backprojection of a CT image.

Slice—a computational cross-section image of an object that is constructed through techniques such as backprojection. A slice is a two-dimensional image.

Projection Data—in fan beam, a projection data set is a collection of projections, each projection representing the measurements of x-rays on a detector. The term projection does not exclude any processing of that data, such as corrections, logarithms, filtering (convolutions), etc.

Sinogram—a set of fan beam projections, each one-dimensional, arranged into an image.

Rendering—this is a process by which the graphics engine is directed to draw a picture based on the settings and data stored on associated memory.

Reconstructed Image—this is the end product of backprojection, and may refer to, for example, a reconstructed slice or a reconstructed volume.

Accumulation Buffer—a frame buffer or other memory associated with the graphics rendering engine.

Volumetric CT (VCT)—is a projection data set, where each projection is a two-dimensional image, comprising many such projections. A cone beam projection set and a helical cone beam projection set are examples of VCTs.

FIG. 1 depicts one example of a diagnostic system in accordance with one aspect of the present invention. This system includes a CT scanner 10 having a stationary gantry 12, which defines an examination region 14. A rotating gantry 16 is mounted on stationary gantry 12 for rotation about the examination region 14. A source of predetermination radiation 20, such as an x-ray tube, is arranged on the rotating gantry 16 for rotation therewith. The source of radiation produces a beam of radiation 22 that passes through the examination region 14 as the rotating gantry 16 rotates. A collimator and shutter assembly 24 forms the beam of radiation 22 into, for example, a thin fan shape, and selectively gates the beam 22 on and off. Alternatively, the radiation beam 22 is gated on and off electronically at the source 20. A subject support 30, such as a table or the like, suspends or otherwise holds a subject being examined or imaged at least partially within the examination region 14 such that the beam of radiation 22 cuts a cross-sectional slice through the region of interest of the subject.

Optionally, the subject is successively repositioned such that neighboring cross-sectional slices are taken in consecutive indexed fashion to produce a three-dimensional volume of slices. Alternately, as is the case with continuous helical CT, concurrently with the rotation of the rotating gantry 16, the support 30, and consequently the subject thereon, are translated along a central horizontal axis of the examination region 14. In this manner, the source 20 follows a helical path relative to the subject. In another embodiment, support 30 remains stationary while the gantry 12 is translated or otherwise moved relative to the subject such that the source 20 follows a helical path relative thereto.

A ring of radiation detectors 40 is mounted peripherally about the examination region 14 on the gantry 12. Alternatively, an arc of radiation detectors 40 could be mounted on the rotating gantry 16 on a side of the examination region 14 opposite the source 20 such that they span the arc defined by the fan-shaped beam of radiation 22. The radiation detectors 40 are arranged to receive the radiation emitted from the source 20 after it has traversed the examination region 14.

In a source fan geometry, an arc of detectors which span the radiation emanating from the source 20 are sampled concurrently at short time intervals as the source 20 rotates behind the examination region 14 to generate a source fan view. In a detector fan geometry, each detector is sampled a multiplicity of times as the source 20 rotates behind the examination region 14 to generate a detector fan view. The paths between the source 20 and each of the radiation detectors 40 are denoted as rays.

The radiation detectors 40 convert the detected radiation into electronic projection data. That is to say, each of the radiation detectors 40 produces an output signal which is proportional to an intensity of received radiation. A difference between the magnitude of radiation received by the reference detector and each radiation detector 40 provides an indication of the amount of radiation attenuation along a corresponding ray of a sampled fan of radiation. In either case, each radiation detector 40 generates data elements which correspond to projections along each ray within the view. Each element of data in the data line is related to a line integral taken along its corresponding ray passing through the subject (or object) being reconstructed.

With detector view geometry, each view or data line represents a fan of rays having its apex at one of the radiation detectors 40 collected over a short period of time as the source 20 rotates behind the examination region 14 from the detector. With source view geometry, each view or data line represents a fan of rays having an apex at the source 20 collected by concurrent sampling of all the radiation detectors 40 spanning the fan of radiation.

A gantry acquisition memory board 50 receives the sampled data from the radiation detectors 40. The gantry acquisition memory board 50 optionally shuffles the data to transform it from a detector fan geometry to a source fan geometry, or vice versa, and performs a ripple filtering operation before passing the data to an image backprojection subsystem 100.

Optionally, for those applications wherein other than parallel projection data is collected, the image backprojection subsystem 100 includes a rebinning processor 110. The electronic data generated by the radiation detectors 40 and sampled by the gantry acquisition memory board 50 is fed to the rebinning processor 110. The rebinning processor 110 converts each data line from its fan-beam or otherwise divergent format to a parallel-beam format. In one embodiment and in the interest of speed and accuracy, this process is optionally broken down into three rebinning operations or steps: an angular view filtering step, an interpolation step which sorts the data into unequally spaced parallel rays, and a final interpolative step that corrects for the unequal spacing of the rays. As explained further below, the use of rebinning processor 110 is optional. For example, a line 90 could be used to feed the raw image data from gantry acquisition memory board 50 to a pre-process stage 140. By doing this, the need for rebinding processor 110 is eliminated, as well as any need for the convolver and preliminary interpolator discussed below. Those skilled in the art will understand that the process flows described below (with reference to FIGS. 2A–6C) can accommodate various types of raw image data (i.e., fan beam, cone beam, helical cone beam, etc.) through the building and application of the projection angle matrix during the rendering of the projection data.

The rebinning processor 110 initially receives the data lines into a first rolling buffer 112. An angular view filter 114 retrieves the data lines from the first rolling buffer 112, filters them, and writes them into a preset position in a second rolling buffer 116. The angular view filter is applied across a plurality of adjacent data lines (for example, 3 to 5) to generate a weighted average thereof. The weighted average is characterized by a centered symmetric non-linear function. Further, at this stage associated view reduction contributes to reduced processing time. Next, an interpolator 118 retrieves and reorders the data stored in the second rolling buffer 116 such that parallel rays from the various data lines are grouped together. Optionally, the number of data lines may be reduced by skipping data lines, for example, every other data line, in order to shorten the data processing time. Further, any corrections common to all the radiation detectors 40 are optionally made at this point. Next, an additional interpolative step is taken to equalize the spacing within each group of parallel data rays. Alternately, any appropriate rebinning processor can be employed.

After parallel projection data has been obtained, it is fed to a convolver 120 which processes the view data and loads it into a preliminary interpolator 130. The convolver 120 performs mathematical manipulations which convolve each view with an appropriate filter or convolution function for the view format, namely parallel. It is noted that in one scanner embodiment, as the source 20 moves, each of the radiation detectors 40 is concurrently generating intensity data. In order to accommodate this rapid flow of information, the convolver 120 may include a plurality of convolvers for convolving several data lines concurrently.

The preliminary interpolator 130, receiving the convolved parallel projection data from the convolver 120, performs a linear or higher order interpolation on selected portions of each data line. Preliminary interpolator 130 performs a higher order interpolation than that used in the backprojection step in order to maintain interpolation precision during backprojection. Only that portion of the projection data defining a zoom backprojection field (i.e., the particular region of interest upon which the backprojection is to be focused) is interpolated and transferred to the backprojection step. Zooming can be accomplished by selecting the appropriate portion of projection data for pre-interpolation. No change in back projection parameters need be employed since parallel beam projections of constant size are being pre-interpolated.

The preliminary interpolator then passes its output to a pre-processor 140 where the resulting projection data set is split into a plurality of multi-channel textures corresponding to the processing channels defined by a multi-color rendering engine 150. In this case, three color channels, red, green and blue are employed. For exemplary purposes, the multi-color rendering engine 150 could be a 24-bit three-color graphics card with eight bits per color channel. However, other multi-color rendering engines for various applications and/or levels of desired precision are possible. The multi-color rendering engine simultaneously and separately renders the projection data of a multi-channel texture to obtain intermediate results for each color channel. This data is then transferred to an accumulation buffer 160 associated with a post processor 180. The data from accumulation buffer 160 is controllably read out for backprojection of the image 170. Alternatively, backprojection processing 170 could directly operate on the outputted data from rendering engine 150 prior to accumulation in the accumulation buffer 160 such that the multi-color channel renderings might be directly recombined as described herein further below. In either case, the resulting image can be scaled and biased for output to an output device 190, such as a display device. Typical displays might include reprojections, selected slices or planes, surface renderings, and the like. Other output devices might comprise a network, a storage device (e.g., writing to a disk in the format of a file), a picture archival system (PACS), or any device capable of storing or displaying output for current or future use.

As described herein, backprojection is achieved by use of graphics hardware commonly used to perform multi-color rendering of objects. By dividing the projection data set between multiple color channels of the rendering engine, enhanced backprojection processing is performed. The examples given herein should not be interpreted as restricting the claimed invention to a particular hardware configuration, beam geometry, or other steps employed in the backprojection process. They are intended to illustrate the steps that permit use of a multi-channel rendering engine for backprojection as claimed herein. Further, although described herein with reference to multiple color channels of a conventional graphics card, the concepts presented are applicable to any hardware or software implemented rendering engine having multiple channels capable of simultaneous processing of projection data organized by the pre-processing logic described herein. Various combinations of precision of rendering engine, projection data, and output image data are possible. Moreover, if desired, the preliminary interpolator 130 can be optionally omitted, as well as the rebinning processor 110 and the convolver 120, with the raw image data fed directly in to the pre-processing system 140. This is possible since the conversion and manipulation of beam geometry can be handled in the projection angle matrix processing discussed below. The image processing concepts presented below are also applicable to other diagnostic imaging apparatus. In an alternate embodiment, a traverse and rotate type CT scanner can provide parallel projection data. In another embodiment, a nuclear or gamma camera could provide the projection data, in either a parallel or divergent format. Optionally, any appropriate diagnostic imaging apparatus which generates projection data can employ the techniques described herein.

Fan-beam backprojection is a process wherein an x-ray source generates a fan-beam through an object onto a detector array. As described above, the source and detector are rotated around the object to collect a sufficient number of projections. FIGS. 2A, 2B & 2C depict a flowchart of one embodiment of a process in accordance with an aspect of the present invention, wherein projection data is stored as multi-channel textures, and then rendered using a multi-channel rendering engine. In accordance with this processing, fast backprojection of a fan-beam slice is achieved by first splitting the raw projection data based on projection angle. Assuming a three-channel rendering engine, a first third of the textures is placed into a first channel, a second third is placed into a second channel, and a final third is placed into a third channel. In one example, these three channels may comprise the red, green and blue color channels of a graphics engine, such as a conventional graphics card. Since each texture represents a projection taken at a progressively increasing angle, the first third of the textures might span a 0° to 120° rotation about the subject (or object), the second third might span projections from, for example, 121° to 240°, and the final third of textures might represent projections from 241° to 360°. The color channels are then simultaneously rendered, thereby producing an image in one third of the time conventionally required. This is achieved by rendering the three textures loaded into the multi-channel rendering engine for all slices at the same time from 0° through 120°. In order to recover the final image, the different results that each channel produces are respectively read out from the accumulator, rotated back to their starting angle (i.e., where applicable), and then recombined.

Note that a three-channel rendering engine and 360° of projection data are presented as examples only. The concepts described can apply to any multi-channel rendering engine, as well as to any degrees of image projection. Generally, data can be divided between channels by taking the total number of projection angles and dividing that number by the total number of channels available. For example, in a system that takes 180° of projection data, and employs a three-channel rendering engine, the data can be divided into thirds such that each channel contains data in increments of 60°. For example, a first channel contains increments from 0° to 60°, a second channel from 61° to 120°, and a third channel from 121° to 180°. Once the data is so divided, then the data is rendered from 0° to 60°, and the results are post-translated to account for the initial 60° and 120° offset to return the data results to their proper geometric coordinates. As another example, in a system that generates 180° of projection data and employs a six-channel rendering engine, the data can be divided into one-sixths, such that each channel contains 30° of data . The resultant texture would be rendered from 0° to 30°, and the results post-translated for the five adjusted channels to their proper position for final image backprojection.

Referring to FIG. 2A, the raw image data (or sinogram) 200 is read 202 and a ramp filter 204 is applied to the projection data. Ramp filtering is conventional processing, also referred to in the art as inverse radon transforming. The technique is well know, and the present invention is not dependent on this filtering step. In this example, the current projection is then split into thirds 306 and a three channel texture is assembled 308. This texture is produced by loading the current angle projection data into, for example, the red channel, by loading the current angle projection data plus 120° offset into the green channel 212, and by loading the current angle projection data plus 240° offset into the blue channel 214.

Figure 4A:
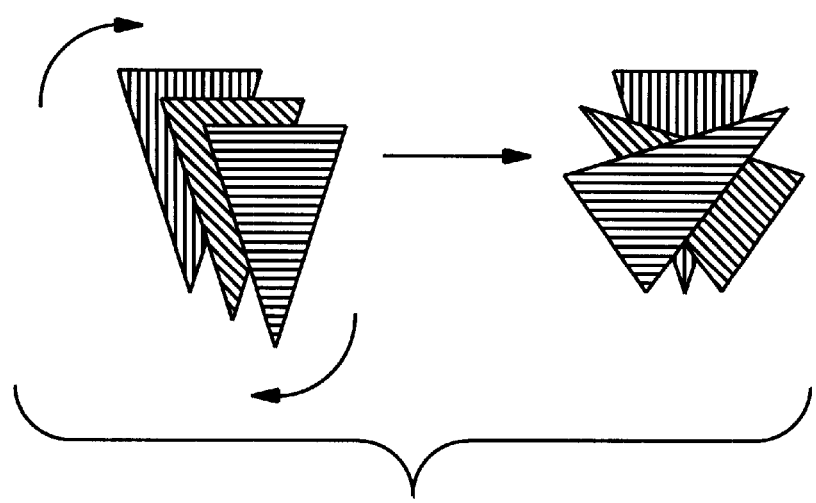
FIG. 4A illustrates texture data rotation for various projection angles in accordance with one embodiment of the tomographic backprojection process of FIGS. 2A, 2B & 2C.

The resulting three channel texture is then loaded into the multi-channel rendering engine 216 and the build process is repeated for one third of the total number of projection angles (e.g., 0°–120°). To restate, assuming that there is 360° of projection data, processing of FIG. 2A splits the sinogram into 120° segments. FIG. 4A is a representation of this concept wherein the different triangles are assumed to represent 120° of projection data. As shown in the left side of the figure, the textures are all rendered simultaneously for the 0°–120°, and then on the right side they are rotated to their correct angles during post processing (described below) before being accumulated. By manipulating the data in this manner, the total number of renderings required per slice is advantageously reduced by two-thirds (i.e., in this three channel example).

As shown in FIG. 2B, the resultant projection angle matrix is loaded into the multi-channel rendering engine 220 and the multi-channel texture associated with a current projection angle is recalled 222. This texture is rendered 224 and the results are accumulated 226 in an accumulation buffer (e.g., a frame buffer associated with the graphics engine). In a three-channel example, the rendering engine repeats this process for only one third of the projection angles of a slice, enabling all of the color channels to be backprojected at once.

Post accumulation, the resultant image is read from the accumulation buffer 230 into, e.g., an RGB array 232. This array is then post processed to adjust for the offset projections in the green and blue channels. In the example presented, the green channel is read and rotated by one-third of the total projection degrees 234, and the blue channel is read and rotated by two-thirds of the total projection degrees 236. The post-rotated data is then added back with the results from the red channel to produce the resultant image 238, which is written to an output device 240. Again, the overall effect of the processing of FIGS. 2A–2C is to improve performance by reducing the total number of renderings required per slice through the multi-channel rendering engine. This concept can be extended to other beam modalities as well.

Cone-beam backprojection describes a process where an x-ray source generates a cone-beam through a subject (or object) onto a detector array. Again, the source and detector are rotated around the object to collect projection data for one full rotation. As described in detail below with reference to FIGS. 3A–3C, it is possible to simultaneously reconstruct several slices of cone-beam data by separating the raw data of each projection into, for example, multiple segments for separate input to a multi-channel rendering engine. Instead of splitting all the projections into multiple channels, as is the case with the fan beam approach, the cone-beam methodology is to split up each volumetric projection into multiple channels. For example, the first third of a volumetric projection might be placed into the red channel, the second third into the green channel, and the final third into the blue channel of an RGB rendering engine. All channels are then rendered simultaneously through all 360° of the projections. When one slice is rendered across all of the channels, three slices are actually generated (in the example). Instead of doing a number of renderings of one slice for a given number of slices, three slices are simultaneously rendered, and only a third the number of slice renderings is needed to reconstruct a volume. The final image is recovered by reading out the color channels from the accumulator, and using the associated slice reference numbers to recombine the color channel outputs. One detailed example of this process is presented in FIGS. 3A–3C. (Note that if the multi-channel rendering engine contains more than three channels, then more slices can be reconstructed by packaging the data into smaller segments equal to the number of channels available on the rendering engine. For example, for a six-channel rendering engine, a volume could be reconstructed in one-sixth of the total number of renderings conventionally needed to complete the slices.)

Referring to FIG. 3A, the raw image data 300 is read to extract projection data 302. A ramp filter 304 is applied to the projection data, and the pixels of the current projection data are split into thirds 306. Again, unlike the fan-beam modality discussed in connection with FIGS. 2A–2C, this cone-beam process splits up each individual projection into three pieces by splitting the pixel data into, e.g., three thirds in order to create a three-channel texture 308. The first third of each projection data is put into, for example, the red channel 310, the second third is assigned to the green channel 312, and the remaining third is assigned to the blue channel 314 of an RGB graphics engine. The three process is repeated for all projections and the resultant channel textures are loaded onto the graphics rendering engine 316, thereby producing the three channel projection angle matrix.

Figure 4B:
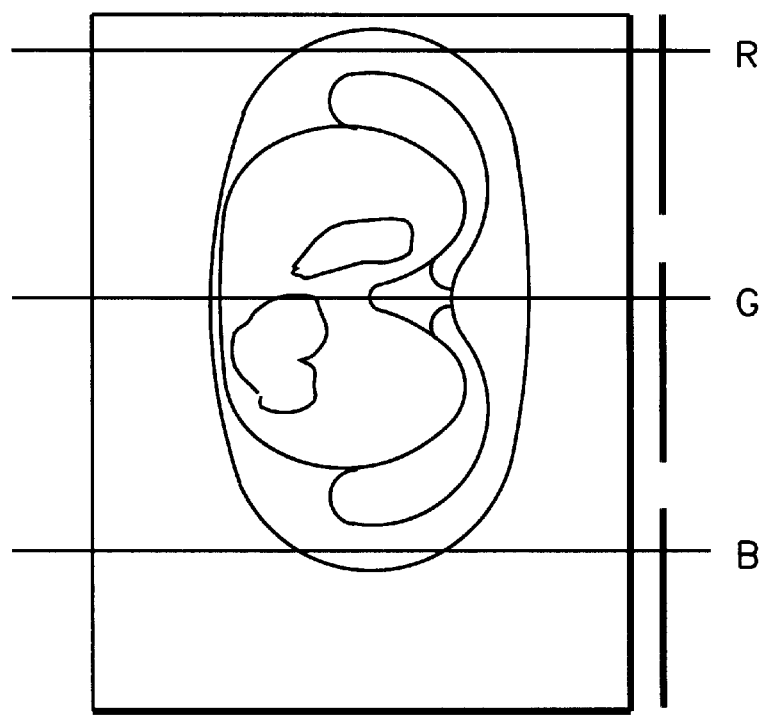
FIG. 4B illustrates splitting texture data of a given projection angle for simultaneous processing through different channels of a multi-channel graphics rendering engine in accordance with one embodiment of the tomographic backprojection process of FIGS. 3A, 3B & 3C.

FIG. 4B is an example of projection data that is split for input into the red, green and blue channels of a multi-channel rendering engine. The cone-beam modality will have two-dimensional projection images which contain multiple slices once reconstructed. Rather than rendering each slice individually, the pixels of the projection data are split into thirds to reduce the number of renderings required by two-thirds.

Rendering engine processing begins by loading the projection angle matrix 320 and recalling a texture associated with a current projection angle 322. The three channel texture is then rendered 324 and the resultant images are separately accumulated in an accumulation buffer 326. The process repeats for all projection angles of the reduced number of slices in the projection angle matrix. Thus, all the channels are rendered at the same time, through all 360° of the projections. When one slice is rendered across the channels, three slices are actually generated.

To achieve a final image post processing is employed, one embodiment of which is depicted in FIG. 3C. As shown, the accumulation buffer data is read out 330 and the RGB data is separated from the buffer 332. This involves reading from the red channel data and writing the data to an output device 334, reading the green channel data and writing the data to an output device 336, and reading the blue channel data and writing the data to an output device 338. During the data reading, slice reference numbers can be employed to recombine the outputs from the color channels.

An alternate technique for enhanced backprojection of fan-beam data could be implemented based on the cone-beam processing described above. For example, several slices of data could be retrieved and distributed among the three color channels. The first third of a projection would be put into the red channel, the second third into the green channel, and the final third into the blue channel. Again, all the channels are rendered at the same time through all 360° of the projections. This technique would be similar to the cone-beam modality process described above, except that fan-beam data would be employed. Fan-beam or cone-beam helical backprojection is also possible, as explained further below. In helical backprojection, instead of the source and detector rotating around an object on a single plane, the source and detector rotate around the object in a helical fashion. More particularly, the source and detector rotate around the object while also moving transverse the object.

Helical backprojection enables the volume scanning of objects too long to scan by circular path methods. By adding a translational movement along an object to the acquisition device's circular movement, a helical path is produced. The helical cone-beam modality is an extension of the circular cone-beam modality with the addition of a translational movement measured by pitch, which is defined as the translational distance traveled during two consecutive turns of the scanner. FIGS. 5A–5C depict a flowchart of one embodiment of a process for tomographic backprojection using texture mapping and a rendering engine for a helical cone-beam modality. One aspect of this process is to maintain the imaging plane camera at a constant distance to the acquisition device. This is achieved by translating and rotating the camera at the same rate as the acquisition device. In circular cone-beam backprojection, the acquisition device moves in a planar circular path, and the imaging plane camera remains at a constant distance from the projection. When implementing helical cone-beam modality, the helical path of the source can be broken off into its two separate paths: the circular path and the translational path orthogonal to the circular path. Moving the imaging plane camera with the projection space allows simplification of the helical cone-beam backprojection problem to essentially the cone-beam backprojection problem, where the imaging plane camera remains at a constant distance from the projection.

Referring first to FIG. 5A, the raw image data 500 is read to extract projection data 502. A pitch angle, which is the angle at which (for example) a patient is moving through the scanner, is read, as well as a number of projections, which may (in one example) be greater than 360° due to translation of the subject relative to the scanner 504. Ramp filtering is applied 506 and the projection data is loaded into a texture 508. A slice distance change between pitch angles is then calculated 510. As one example, this slice distance change between pitch angles may equal a constant multiplied by the pitch angle that is read divided by the total number of projections. The constant is a number that maps the projection space to the model space, and is dependent on the graphics environment's geometrical setup and can be readily obtained by one skilled in the art through experimentation. The slice distance change between pitch angles represents how much distance the model space moves between projections. This distance change is employed to translate the model space plane to maintain the distance to the projection space constant.

As shown in FIG. 5B, the rendering engine employs the resultant projection angle matrix 520 to, for each projection angle of each slice, recall a texture 522 associated with the current projection angle. The model space is then adjusted for the constant slice distance previously calculated 524. The texture is rendered 526 and accumulated in an accumulation buffer 528. This process is repeated for each projection angle in the projection angle matrix.

processing reads out the accumulation buffer data 530 and writes the resulting data to an output device 532, as shown in FIG. 5C.

Tomographic backprojection of helical cone-beam projection data can be further optimized by separately using the channels of a multi-channel rendering engine in a manner similar to that described in connection with the cone-beam modality of FIGS. 3A–3C. A flowchart of one example of this process is presented in FIGS. 6A–6C.

Referring first to FIG. 6A, the raw image data 600 is employed to calculate pixel distance between pitch angles 602 in a manner similar to that described above in connection with process 510 of FIG. 5A. The projection data is read from the helical cone acquisition 604 and the pitch angle information and number of projections 606 are obtained. A conventional ramp filter is optionally applied 608 to the projection data, which is followed by building of a multi-channel texture 610. The multi-channel texture 610 employs a shifting to ensure that the same projection image pixel value gets mapped to the correct texture pixel value, across different angles. Using the pixel distance shift between pitch angles, the projection image pixel is shifted over and put into the correct texture pixel location. In the case where the pixel distance shift between angles is a non-integer, basic linear interpolation is used. For example, if the shift is 0.75 and the pixel value for the texture is between a projection pixel of 200 and a pixel of 100, the interpolated value of 175 can be used for the texture pixel. Building the three-channel texture 610 includes loading a first third of data into the red channel, shifted by the appropriate pixel distance 612, loading a second third of data into the green channel, shifted by an appropriate pixel distance 614, and loading the remaining third of data into the blue channel, shifted by the appropriate pixel distance 616. The geometrical distance shift between pitch angles is then calculated 618. This geometrical distance shift between angles can comprise a constant multiplied by the pitch angle divided by the total number of projections. The constant is a value which maps the projection space to the model space, and again, is dependent on the graphics environment's geometrical setup and can be readily obtained by one skilled in the art from the implementer's representation of the virtual geometry of the actual system.

The rendering engine next renders the projection data by first loading the projection angle matrix 620 and, for all slices and projection angles, recalling a texture associated with a current projection angle 622. The model space is thereafter translated by the geometrical distance shift previously determined 624. This translation refers to moving the model in the same direction as the projection. In the same way that the projection angle matrix accounts for the rotation of the helical scanner, the translation by the geometrical distance shift accounts for movement of the helical scanner across the scanned object. The helical motion of the scanner is again broken down into its two rotation and translation components. The texture is rendered 626 and the resultant images are accumulated in an accumulation buffer 628. The process is repeated for a next multi-channel texture of a next projection angle.

Post rendering, the accumulated image data is read out from the accumulation buffer 630 and, using the associated slice reference numbers, written to an output device 632, for example, for storage or display.

The present invention can be included in an article of manufacture (e.g., one or more computer program products) having, for instance, computer usable media. The media has embodied therein, for instance, computer readable program code means for providing and facilitating the capabilities of the present invention. The article of manufacture can be included as part of a computer system or sold separately.

Additionally, at least one program storage device readable by a machine, tangibly embodying at least one program of instructions executable by the machine to perform the capabilities of the present invention can be provided.

The flow diagrams depicted herein are just examples. There may be many variations to these diagrams or the steps (or operations) described therein without departing from the spirit of the invention. For instance, the steps may be performed in a differing order, or steps may be added, deleted or modified. All these variations are considered a part of the claimed invention.

Although preferred embodiments have been depicted and described in detail herein, it will be apparent to those skilled in the relevant art that various modifications, additions, substitutions and the like can be made without departing from the spirit of the invention and these are therefore considered to be within the scope of the invention as defined in the following claims.

What is claimed is:

1. A method of image backprojection from a projection data set comprising:

splitting the projection data set into a plurality of multi-channel textures, each multi-channel texture corresponding to a predetermined number of color channels of a multi-color rendering engine;

simultaneously rendering the split projection data set using the color channels of the multi-color rendering engine to obtain intermediate results for each color channel; and accumulating the intermediate results of each color channel to generate separate rendered images, wherein multiple images are simultaneously rendered from the projection data set using the separate color channels of the multi-color rendering engine.

2. The method of claim 1, wherein the projection data set comprises at least one of parallel beam data, fan beam data, cone beam data, helical fan beam data, and helical cone beam data.

3. The method of claim 1, further comprising combining the separate rendered images to produce a reconstructed image.

4. The method of claim 3, wherein the reconstructed image comprises a reconstructed slice or a reconstructed volume.

5. The method of claim 1, wherein the splitting comprises employing projection angles associated with the projection data set to split the projection data set into the plurality of multi-channel textures.

6. The method of claim 1, wherein the projection data set comprises fan beam data, and wherein said splitting further comprises rotating at least some of the fan beam data using projection angles associated with the fan beam data to create at least one multi-channel texture for loading into the predetermined number of color channels of the multi-color rendering engine, and wherein said method further comprises backrotating at least one of the separate rendered images to compensate for the initial rotating of the at least some fan beam data when forming the at least one multi-channel texture, and thereafter, combining the separate rendered images to produce a reconstructed image.

7. The method of claim 6, wherein the predetermined number of color channels comprises three color channels, and the method further comprises loading at least one multi-channel texture into the three color channels, the loading comprising loading at least some projection angle data thereof into a first channel of the three color channels, rotating by 120° and loading at least some projection angle data thereof into a second channel of the three color channels, and rotating by 240° and loading at least some projection angle data thereof into a third channel of the three color channels.

8. The method of claim 1, wherein the projection data set comprises cone beam data, and wherein the splitting comprises splitting the cone beam data into said plurality of multi-channel textures, and wherein when said rendering renders a slice, said accumulating of the intermediate results produces multiple simultaneously rendered slices.

9. The method of claim 1, wherein the projection data set comprises helical beam data, and wherein the splitting further comprises, for at least one multi-channel texture, determining a geometrical distance change between pitch angles using at least some of the plurality of multi-channel textures, and said simultaneously rendering includes adjusting a model space for rendering texture data associated with at least one current projection angle for a constant texture shift using the geometrical distance change between pitch angles, and wherein the accumulating further comprises accumulating the separate rendered images to produce a helical beam reconstructed image.

10. The method of claim 1, further comprising using a general purpose computer graphics and imaging computer to perform said simultaneously rendering of the split projection data set, said general purpose computer graphics and imaging computer having said predetermined number of color channels.

11. A diagnostic imaging method comprising:
generating a projection data set; and
reconstructing an image from the projection data set, said reconstructing comprising:
splitting the projection data set into a plurality of multi-channel textures, each multi-channel texture corresponding to a predetermined number of color channels of a multi-color rendering engine;
simultaneously rendering the split projection data set using the color channels of the multi-color rendering engine to obtain intermediate results for each color channel; and
accumulating the intermediate results of each color channel to generate separate rendered images, wherein multiple images are simultaneously rendered from the projection data set using the separate color channels of the multi-color rendering engine.

12. The method of claim 11, wherein the projection data set comprises fan beam data, and wherein said splitting further comprises rotating at least some of the fan beam data using projection angles associated with the fan beam data to create at least one multi-channel texture for loading into the predetermined number of color channels of the multi-color rendering engine, and wherein said reconstructing further comprises backrotating at least one of the separate rendered images to compensate for the initial rotating of the at least some fan beam data when forming the at least one multi-channel texture, and thereafter, combining the separate rendered images to produce a reconstructed image.

13. The method of claim 11, wherein the projection data set comprises cone beam data, and wherein the splitting comprises splitting the cone beam data into said plurality of multi-channel textures without reference projection angles associated with the cone beam data, and wherein when said rendering renders a slice, said accumulating of the intermediate results produces multiple simultaneously rendered slices.

14. The method of claim 11, wherein the projection data set comprises helical beam data, and wherein the splitting further comprises, for at least one multi-channel texture, determining a geometrical distance change between pitch angles using at least some of the plurality of multi-channel textures, and said simultaneously rendering includes adjusting a model space for rendering texture data associated with at least one current projection angle for a constant texture shift using the geometrical distance change between pitch angles, and wherein the accumulating further comprises accumulating the separate rendered images to produce a helical beam reconstructed image.

15. A method of image backprojection from helical beam projection data comprising:
loading the projection data into multiple textures;
for at least one texture, determining a texture distance change between pitch angles using at least some textures of the multiple textures;
rendering the multiple textures using a graphics rendering engine, said rendering including adjusting a model space for rendering texture data associated with at least one projection angle for a constant texture distance using the determined texture distance change between pitch angles; and
accumulating rendered images to produce a helical beam reconstructed image from the helical beam projection data.

16. The method of claim 15, wherein the rendering includes using a general purpose computer graphics and imaging computer to perform said rendering.

17. A diagnostic imaging method comprising:
generating a projection data set comprising helical beam data; and
reconstructing an image from the helical beam data, said reconstructing comprising:
loading the helical beam data into multiple textures;
for at least one texture, determining a texture distance change between pitch angles using at least some textures of the multiple textures;
rendering the multiple textures using a graphics rendering engine, said rendering including adjusting the model space for rendering texture data associated with at least one projection angle for a constant texture distance using the determined texture distance change between pitch angles; and accumulating rendered images to produce a helical beam reconstructed image.

18. A system for image backprojection from a projection data set comprising:

pre-rendering means for splitting the projection data set into a plurality of multi-channel textures;

multi-color rendering means for simultaneously rendering the split projection data set using a predetermined number of color channels of the multi-color rendering means to obtain intermediate results for each color channel, wherein at least one multi-channel texture corresponds to the predetermined number of color channels of the multi-color rendering means; and post-rendering means for accumulating the intermediate results of each color channel to generate separate rendered images, wherein multiple images are simultaneously rendered from the projection data set using the separate color channels of the multi-color rendering means.

19. The system of claim 18, wherein the projection data set comprises at least one of parallel beam data, fan beam data, cone beam data, helical fan beam data, and helical cone beam data.

20. The system of claim 18, wherein the post-rendering means further comprises means for combining the separate rendered images to produce a reconstructed image.

21. The system of claim 20, wherein the reconstructed image comprises a reconstructed slice or a reconstructed volume.

22. The system of claim 18, wherein the pre-rendering means further comprises means for employing projection angles associated with the projection data set to split the projection data set into the plurality of multi-channel textures.

23. The system of claim 18, wherein the projection data set comprises fan beam data, and wherein said pre-rendering means further comprises means for rotating at least some of the fan beam data using projection angles associated with the fan beam data to create at least one multi-channel texture for loading into the predetermined number of color channels of the multi-color rendering engine, and wherein said post-rendering means further comprises means for backrotating at least one of the separate rendered images to compensate for the initial rotating of the at least some fan beam data when forming the at least one multi-channel texture, and thereafter, for combining the separate rendered images to produce a reconstructed image.

24. The system of claim 23, wherein the predetermined number of color channels comprises three color channels, and the pre-rendering means further comprises means for loading at least one multi-channel texture into the three color channels, the loading comprising loading at least some projection angle data thereof into a first channel of the three color channels, rotating by 120° and loading at least some projection angle data thereof into a second channel of the three color channels, and rotating by 240° and loading at least some projection angle data thereof into a third channel of the three color channels.

25. The system of claim 18, wherein the projection data set comprises cone beam data, and wherein the pre-rendering means comprises means for splitting the cone beam data into said plurality of multi-channel textures, and wherein when said rendering means renders a slice, said post-rendering means accumulates the intermediate results to produce multiple simultaneously rendered slices.

26. The system of claim 18, wherein the projection data set comprises helical beam data, and wherein the pre-rendering means further comprises, for at least one multi-channel texture, means for determining a geometrical distance change between pitch angles using at least some of the plurality of multi-channel textures, and said multi-color rendering means includes means for adjusting a model space for rendering texture data associated with at least one current projection angle for a constant texture shift using the geometrical distance change between pitch angles, and wherein the post-rendering means further comprises means for accumulating the separate rendered images to produce a helical beam reconstructed image.

27. The system of claim 18, wherein the multi-color rendering means comprises a general purpose computer graphics and imaging computer to perform said simultaneously rendering of the split projection data set, said general purpose computer graphics and imaging computer having said predetermined number of color channels.

28. A diagnostic imaging system comprising:

scanner means for generating a projection data set; and image backprojection means for reconstructing an image from the projection data set, said image backprojection means comprising:

pre-rendering means for splitting the projection data set into a plurality of multi-channel textures;

multi-color rendering means for simultaneously rendering the split projection data set using a predetermined number of color channels of the multi-color rendering means to obtain intermediate results for each color channel, wherein each multi-channel texture corresponds to the predetermined number of color channels of the multi-color rendering means; and post-rendering means for accumulating the intermediate results of each color channel to generate separate rendered images, wherein multiple images are simultaneously rendered from the projection data set using the separate color channels of the multi-color rendering means.

29. The system of claim 28, wherein the projection data set comprises fan beam data, and wherein said pre-rendering means further comprises means for rotating at least some of the fan beam data using projection angles associated with the fan beam data to create at least one multi-channel texture for loading into the predetermined number of color channels of the multi-color rendering engine, and wherein said post-rendering means further comprises means for backrotating at least one of the separate rendered images to compensate for the initial rotating of the at least some fan beam data when forming the at least one multi-channel texture, and thereafter, for combining the separate rendered images to produce a reconstructed image.

30. The system of claim 28, wherein the projection data set comprises cone beam data, and wherein the pre-rendering means comprises means for splitting the cone beam data into said plurality of multi-channel textures without reference projection angles associated with the cone beam data, and wherein when said rendering renders a slice, said post-rendering means comprises accumulating the intermediate results to produce multiple simultaneously rendered slices.

31. The system of claim 28, wherein the projection data set comprises helical beam data, and wherein the pre-rendering means further comprises, for at least one multi-channel texture, means for determining a geometrical distance change between pitch angles using at least some of the plurality of multi-channel textures, and said rendering means includes means for adjusting a model space for rendering texture data associated with at least one current projection angle for a constant texture shift using the geometrical distance change between pitch angles, and wherein the post-rendering means further comprises means for accumulating the separate rendered images to produce a helical beam reconstructed image.

32. A system for image backprojection from helical beam projection data, said system comprising:
   pre-rendering means for loading the projection data into multiple textures, and for at least one texture, for determining a texture distance change between pitch angles using at least some textures of the multiple textures;
   graphics rendering means for rendering the multiple textures, said rendering including adjusting a model space for rendering texture data associated with at least one projection angle for a constant texture distance using the determined texture distance change between pitch angles; and
   post-rendering means for accumulating rendered images to produce a reconstructed image from the helical beam projection data.

33. The system of claim 32, wherein the graphics rendering means comprises a general purpose computer graphics and imaging computer.

34. A diagnostic imaging system comprising:
   scanner means for generating helical beam projection data; and
   image backprojection means for reconstructing an image from the helical beam projection data, said image backprojection means comprising:
      pre-rendering means for loading the projection data into multiple textures, and for at least one texture, for determining a texture distance change between pitch angles using at least some textures of the multiple textures;
      graphics rendering means for rendering the multiple textures, said rendering including adjusting a model space for rendering texture data associated with at least one projection angle for a constant texture distance using the determined texture distance change between pitch angles; and
      post-rendering means for accumulating rendered images to produce a reconstructed image from the helical beam projection data.

35. At least one program storage device readable by a machine, tangibly embodying at least one program of instructions executable by the machine to perform a method of image backprojection from a projection data set, said method comprising:
   splitting the projection data set into a plurality of multi-channel textures, each multi-channel texture corresponding to a predetermined number of color channels of a multi-color rendering engine;
   simultaneously rendering the split projection data set using the color channels of the multi-color rendering engine to obtain intermediate results from each color channel; and
   accumulating the intermediate results of each color channel to generate separate rendered images, wherein multiple images are simultaneously rendered from the projection data set using the separate color channels of the multi-color rendering engine.

36. The at least one program storage device of claim 35, wherein the projection data set comprises at least one of parallel beam data, fan beam data, cone beam data, helical fan beam data, and helical cone beam data.

37. The at least one program storage device of claim 35, further comprising combining the separate rendered images to produce a reconstructed image, wherein the reconstructed image comprises a reconstructed slice or a reconstructed volume.

38. The at least one program storage device of claim 35, wherein the splitting comprises employing projection angles associated with the projection data set to split the projection data set into the plurality of multi-channel textures.

39. The at least one program storage device of claim 35, wherein the projection data set comprises fan beam data, and wherein said splitting further comprises rotating at least some of the fan beam data using projection angles associated with the fan beam data to create at least one multi-channel texture for loading into the predetermined number of color channels of the multi-color rendering engine, and wherein said method further comprises backrotating at least one of the separate rendered images to compensate for the initial rotating of the at least some fan beam data when forming the at least one multi-channel texture, and thereafter, combining the separate rendered images to produce a reconstructed image.

40. The at least one program storage device of claim 35, wherein the projection data set comprises cone beam data, and wherein the splitting comprises splitting the cone beam data into said plurality of multi-channel textures, and wherein when said rendering renders a slice, said accumulating of the intermediate results produces multiple simultaneously rendered slices.

41. The at least one program storage device of claim 35, wherein the projection data set comprises helical beam data, and wherein the splitting further comprises, for at least one multi-channel texture, determining a geometrical distance change between pitch angles using at least some of the plurality of multi-channel textures, and said simultaneously rendering includes adjusting a model space for rendering texture data associated with at least one current projection angle for a constant texture shift using the geometrical distance change between pitch angles, and wherein the accumulating further comprises accumulating the separate rendered images to produce a helical beam reconstructed image.

42. At least one program storage device readable by a machine, tangibly embodying at least one program of instructions executable by the machine to perform a method for image backprojection from helical beam projection data, said method comprising:
   loading the projection data into multiple textures;
   for at least one texture, determining a texture distance change between pitch angles using at least some textures of the multiple textures;
   rendering the multiple textures using a graphics rendering engine, said rendering including adjusting a model space for rendering texture data associated with at least one projection angle for a constant texture distance using the determined texture distance change between pitch angles; and
   accumulating rendered images to produce a helical beam reconstructed image from the helical beam projection data.

* * * * *